United States Patent
Stange et al.

(10) Patent No.: US 7,943,154 B2
(45) Date of Patent: May 17, 2011

(54) METHOD FOR PRODUCING MULTIPLE EMULSIONS THAT ARE STABLE IN STORAGE

(75) Inventors: Olaf Stange, Saulheim (DE); Martina Mutter, Köln (DE); Tanja Oswald, Hagen (DE); Mark Schmitz, Gladbach (DE)

(73) Assignee: Bayer Technology Services GmnH, Leverkusen (DE)

( * ) Notice: Subject to any disclaimer, the term of this patent is extended or adjusted under 35 U.S.C. 154(b) by 1051 days.

(21) Appl. No.: 10/578,329

(22) PCT Filed: Oct. 29, 2004

(86) PCT No.: PCT/EP2004/012275
§ 371 (c)(1),
(2), (4) Date: Mar. 12, 2007

(87) PCT Pub. No.: WO2005/046635
PCT Pub. Date: May 26, 2005

(65) Prior Publication Data
US 2007/0253986 A1     Nov. 1, 2007

(30) Foreign Application Priority Data
Nov. 5, 2003 (DE) .................................. 103 51 644

(51) Int. Cl.
*A61K 9/113* (2006.01)
*A61K 39/00* (2006.01)
*C09K 3/00* (2006.01)

(52) U.S. Cl. ............ 424/283.1; 514/939; 514/937; 516/54; 424/400; 424/184.1; 424/204.1; 424/234.1

(58) Field of Classification Search .............. None
See application file for complete search history.

(56) References Cited

U.S. PATENT DOCUMENTS 6,251,407 B1 * 6/2001 Ganne ................. 424/278.1
6,835,396 B2 * 12/2004 Brynjelsen et al. ........ 424/450
(Continued)

FOREIGN PATENT DOCUMENTS
DE     19630176    *   1/1998
(Continued)

OTHER PUBLICATIONS

Forster et al. Production of fine disperse and long-term stable oil-in-water emulsion by the phase inversion temperature method. Journal of Dispersion Science and Technology, 1992, vol. 13, No. 2, 183-193.*
(Continued)

*Primary Examiner* — Mary E Mosher
*Assistant Examiner* — Stuart W Snyder
(74) *Attorney, Agent, or Firm* — Baker Donelson Bearman Caldwell & Berkowitz

(57) ABSTRACT

A process is described for the preparation of storage-stable, multiple emulsions of the water/oil/water (W/O/W) type which comprise one or more active ingredients.
The process comprises the steps
  a) stirring the active ingredient into an aqueous phase,
  b) emulsifying the aqueous phase by passing the aqueous phase through a large-pored, porous membrane into an oil phase,
  c) phase inversion of the emulsion from b), by cooling the mixture at a cooling rate of at least 0.3 K/min, where an emulsifier is added either to the aqueous phase in a) or to the oil phase in b) or to both phases.

18 Claims, 2 Drawing Sheets

U.S. PATENT DOCUMENTS

2002/0051748 A1    5/2002    Snow et al.

FOREIGN PATENT DOCUMENTS

| | | |
|---|---|---|
| EP | 0481982 | 4/1992 |
| EP | 0489181 | 6/1992 |
| EP | 0564738 | 10/1993 |
| WO | WO 90/00150 | 1/1990 |

OTHER PUBLICATIONS

Higashi et al. Size of lipid microdroplets effects results of hepatic arterial chemotherapy with an anticancer agent in water-in-oil-in-water emulsion to hepatocelluar carcinoma. The Journal of Pharmacology and Experimental Therapeutics, 1999, vol. 289, No. 2, 816-819.*

Joscelyne et al. Membrane emulsification—a literature review. Journal of Membrane Science, 2000, vol. 169, 107-117.*

Encyclopedia of Pharmaceutical Technology, vol. 3. James Swarbrick. Informa Healthcare USA, Inc. NY, NY. © 2007, p. 1561.*

Hideaki Okochi, et al., Preparation and Evaluation of w/o/w Type Emulsions Containing Vancomycin; Advanced Drug Delivery Reviews, vol. 45 (2000), pp. 5-26.

Terrise, I.; M. Seiller, et al. "Multiple W/O/W emulsions, theoretical study" (1992). Congr. Int. Technol. Pharm., 6th 4: 328-35.

Joscelyne, S.M. and G. Tragardh (2000), "Membrane emulsification—a literature review". J. Membr. Sci 169 (1): 107-117.

* cited by examiner

METHOD FOR PRODUCING MULTIPLE EMULSIONS THAT ARE STABLE IN STORAGE

CROSS-REFERENCE TO RELATED APPLICATIONS

The application is a §371 National Stage Application of International Application No. PCT/EP04/012275 filed Oct. 29, 2004 which claims priority to German Application No. 10351644.1 filed Nov. 5, 2003.

BACKGROUND OF THE INVENTION

1. Field of the Invention

The present invention relates to a process for the preparation of a stable multiple emulsion of the water/oil/water (WOW) type, where the external phase and also the internal aqueous phase can comprise a pharmaceutical active ingredient, and whose oil-containing phase comprises a nonionic surfactant which acts as emulsifier. This multiple emulsion is prepared by introducing the aqueous phase into the oil phase through a porous membrane and then cooling the water-in-oil (W/O) emulsion to form the abovementioned W/O/W double emulsion, which is used in particular for veterinary medicinal purposes.

2. Description of Related Art

Multiple emulsions are emulsions of emulsions which can primarily be present in two types, namely W/O/W emulsions and O/W/O emulsions. These systems are of great interest in many areas of application. They permit firstly protection of the active substances in the innermost phase, and secondly the incorporation of two active substances which react with one another into two phases of the same formulation. Furthermore, prolonged effectiveness of the active ingredients in the innermost phase can be observed following administration to organisms.

Nowadays, however, there are only a few multiple emulsions in medicine and cosmetics since their formulation and their stability still present a problem and the phenomena of emulsification have still not been completely explained. The principles are given in "Multiple W/O/W emulsions, theoretical study" Terrise, I.; M. Seiller, et al. (1992). Congr. Int. Technol. Pharm., 6th 4: 328-35.

In veterinary medicine, vaccines are required to immunize against one or more pathogens in which the active ingredient is present in the vaccine in as finely distributed a form as possible and spreads within the animal in particular over a prolonged period.

Multiple emulsions represent an interesting emulsions system for use in the vaccine formulation. They are emulsions which, in the innermost phase, comprise relatively small drops of a liquid which corresponds to the continuous outermost phase. One way of formulating such a vaccine is the multiple W/O/W emulsion. Here, the active ingredient is found, for example, in the form of an insoluble protein of a certain particle size in the aqueous innermost phase. As a result of the additional oil phase, uptake into the body is delayed, and thus the effectiveness is prolonged. Furthermore, the oil acts in some instances as an adjuvant, i.e. it can boost the antigenic effect of the vaccine.

Formulation in the form of multiple emulsions is also known from the field of cosmetics. Laid-Open Specification DE 196 30 176 A1 describes the composition of the ingredients, and the preparation of such double emulsions with the help of phase inversion.

The patent specification U.S. Pat No. 6,251,407 B1 describes a composition of oil, emulsifier, aqueous phase and pharmaceutical active ingredient which can be used for preparing a vaccine. In this, the individual constituents can be described in more detail as follows: the oil used is a so-called self-emulsifying oil which consists of polyglycolized glycerides. The aqueous phase comprises an active ingredient which is an antigen.

This double emulsion according to EP-A-489 181 or EP-A-481 982 is prepared by the "stirring" of the aqueous active ingredient-containing phase into an oily phase, and subsequent phase inversion to form a double emulsion by temperature gradients and subsequent homogenization by stirring.

The disadvantage of the W/O/W emulsion which is produced here as in the case given above is the inhomogeneous broad droplet distribution and the poor reproducibility of the droplet distribution in the finished emulsion with different stirred-tank reactor geometries. Furthermore, this process is only possible in discontinuous operation.

Furthermore, processes for producing multiple emulsions with membranes are already known. The literature source Joscelyne, S. M. and G. Tragardh (2000), "Membrane emulsification—a literature review". J. Membr. Sci 169 (1): 107-117 describes this in detail. Here, an aqueous phase, for example, is introduced into one of the phases via a membrane. The droplet size corresponds to 2 to 10 times the pore diameter of the membrane. Limitations arise from the limiting of the particle size by the radius of the membrane pore. However, it has been found that the diameter of the membrane pore has a detrimental effect on the incorporation of an active ingredient into the emulsion if the active ingredient particle is too large.

The patent application EP 564 738 A1 a membrane process for the preparation of emulsions in which a first emulsion is effected by membrane emulsification, generation of the double emulsion is effected by stirring, or both are effected by membrane emulsification. The process serves to prepare in steps a low-fat spread in the form of a double emulsion which is characterized by economizing on stabilizers and gel formers. The final emulsion drops therein have an average diameter of from 10 to 16 μm.

All of the specified processes are only appropriate for one field of application and cannot therefore be simply transferred to further fields of use.

SUMMARY OF THE INVENTION

The object of the invention is to form a stable double emulsion of the 1) W/O/W type where the external phase and/or the internal aqueous phase comprises a pharmaceutical active ingredient, e.g. in the form of an antigen, and whose oil-containing phase comprises a surfactant which acts as emulsifier.

The droplet size of the oil phase here should, in particular, not exceed the average diameter of 3 μm, that of the internal aqueous phase of 0.3 μm. In addition, the process should, in particular, have a narrower particle size distribution and consequently higher reproducibility than conventional processes.

The problem also arises that the active ingredient particles present in heterogeneous and partially agglomerated form are not separated, for example, by the membrane used, or destroyed by shearing due to their size.

Surprisingly, it has been found, and herein lies the attainment of the object, that the abovementioned, storage-stable multiple emulsions of the W/O/W type can be formed by the following process, which is the subject-matter of the invention:

a) stirring the active ingredient into an aqueous phase,
b) emulsifying the aqueous phase by passing the aqueous phase through a large-pored, porous membrane into an oil phase,
c) phase inversion of the emulsion from b), by cooling the mixture at a cooling rate of at least 0.3 K/min, preferably at least 1 k/min, where an emulsifier is added either to the aqueous phase in a) or to the oil phase in b) or to both phases.

BRIEF DESCRIPTION OF THE FIGURES

The Figures show.

DETAILED DESCRIPTION OF A PREFERRED EMBODIMENT

Figure 1:
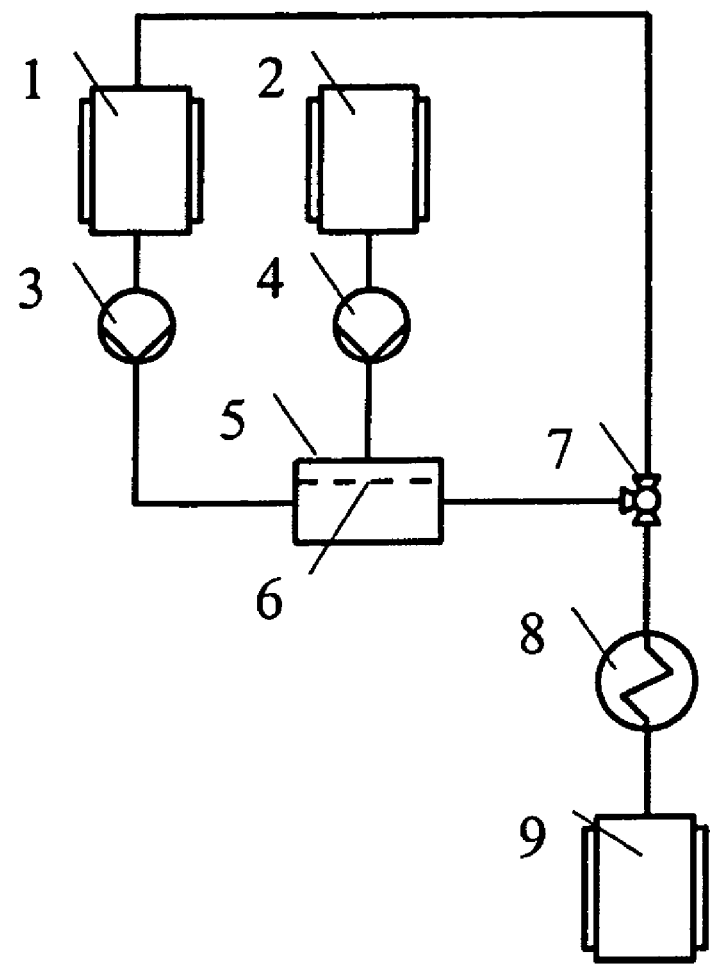
FIG. 1 Diagrammatic representation of the experimental plant used in the example
FIG. 2 Scheme of a multistage plant for carrying out the process.

The simple emulsion is formed, for example, by the stirring method known in principle. The droplet size (number-average) is typically between 10 and 30 μm, and the said phase inversion temperature is generally 60 to 90° C.

For the process according to the invention, preference is given to using porous inorganic membranes, particularly preferably ceramic membranes, in particular of $Al_2O_3$, $ZrO_2$, $TiO_2$ and mixtures of these oxides, particularly preferably of $Al_2O3$.

The pore size of the membrane is, on average, preferably 0.2 μm to 5 μm, particularly preferably 0.3 μm to 3 μm.

Suitable ingredients for the continuous phase are, for example, generally oils, and for the discontinuous phase, for example, aqueous solutions, in particular liquids which are immiscible with the continuous phase. As oil phase, preference is given to using mineral oil, white oil or vegetable oil.

A further essential component is the emulsifier, which is initially introduced into the aqueous phase a) and/or oil-containing phase b), depending on the composition, in the preferred process it is present in the form of a nonionic emulsifier in the oil phase b).

The process is particularly preferably carried out in a temperature range with regard to the emulsification according to step b) of from 30° C. to 35° C., and with regard to the phase inversion a temperature gradient of 30K, but at least of 15K.

It has been found that using the process, an extremely narrow particle size distribution and an average particle diameter (oil phase) of from 1 μm to 3 μm can be achieved through appropriate choice of the feed materials and operating conditions.

The active ingredient initially introduced into the aqueous, i.e. in particular discontinuous, phase may, for example, be a pharmaceutical active ingredient, preferably for veterinary purposes, in particular an antigen for a vaccine formulation.

The active ingredient is preferably chosen from the series:
An antigen, such as, for example, a virus, a microorganism, specifically a bacterium or parasite, or a preparation consist which comprises a peptide chain. This preparation may a protein or a glycoprotein, particularly a protein or a glycoprotein which has been obtained from a microorganism, a synthetic peptide or a protein or peptides which has been produced by genetic manipulation.

The abovementioned virus and/or microorganism can be completely deactivated, live or attenuated.

Viruses which represent antigens which may be mentioned are preferably: rabies virus, Aujeszky's virus, influenza viruses, foot-and-mouth virus and HIV viruses.

Microorganisms or types of bacteria which are antigens which may be mentioned are preferably: *E. coli* and the strains *Pasteurella, Furonculosis, Vibriosis, Staphylococcus* and *Streptococcus*.

Parasites which may be mentioned are preferably the strains *Trypanosoma, Plasmodium* and *Leishmania*.

The pressure difference over the membrane (transmembrane pressure) is preferably $0.5*10^5$ Pa to $25*10^5$ Pa, but preferably $0.5*10^5$ Pa to $5*10^5$ Pa, depending on the concentration of active ingredient in the discontinuous aqueous phase.

The process can in principle be carried out continuously or batchwise.

The process is preferably carried out continuously in all steps.

The continuous phase preferably flows over at between 0.5 and 5 m/s, particularly preferably between 1 and 3 m/s. The disperse phase flux of the discontinuous phase through the membrane is in particular from 50 to 1500 $l/(m^{2*}h)$, preferably from 800 to 1200 $l/(m^{2*}h)$.

The discontinuous phase, which forms the basis of the invention, consists preferably of an electrolyte, which preferably a combination of weak acids and weak bases, weak acids and strong bases or strong acids and weak bases.

The electrolytes particularly preferably comprise one or more of the following compounds:
boric acid, phosphoric acid, N-2-(acetamido)-2-aminoethanesulphonic acid, N-2-(acetamido)-2-iminodiacetic acid, alanine, 2-amino-2-methyl-1,3-propanediol, ammonia, N,N-bis(2-hydroxyethyl)-2-aminoethanesulphonic acid, N,N-bis(2-hydroxyethyl)glycine, 2,2-bis(hydroxyethyl)iminotris(hydroxymethyl)methane, 2-(cyclohexylamino)ethanesulphonic acid, 3-[4-(2-hydroxyethyl)l-piperazinyl]-propanesulphonic acid, histidine, imidazole, lactic acid, 2-morpholinoethane-sulphonic acid, 2-morpholinopropanesulphonic acid, piperazine-1,4-bis(2-ethane-sulphonic acid), N-[tris(hydroxymethyl)methyl]-2-aminoethanesulphonic acid, N-[tris(hydroxymethyl) methyl]glycine, triethanolamine, tris(hydroxymethyl) amino-methane, citric acid.

The process can in principle be operated in sterile conditions.

The process can also be modified in as much as a plurality of different discontinuous aqueous phases with various ingredients are metered in over a plurality of different membranes at different points of the oil phase. This is particularly advantageous if the individual active ingredients have mutual incompatibility or reactivity with one another.

An advantageous secondary effect of the process is the use of the membrane as emulsification membrane on the one hand and filtration means on the other hand, for example for separating off undesired agglomerates, impurities or excessively large active ingredient particles which have a larger diameter than the pores of the membrane and can adversely affect the quality of the desired product.

The separation of abovementioned undesired secondary components can be realised in one process step just as much as in a multistage process.

The membrane filtration following membrane emulsification can also serve for concentrating and/or demineralizing the product.

The described invention is particularly suitable in animal health for the formulation of vaccines by preparation methods described above, and likewise for the formulation of pharmaceutical active ingredients in human medicine which are characterized by a favourable presentation and adaptable controlled release properties.

The examples below relate to advantageous embodiments according to the invention. The numerical values are all percentages by weight, based on the total weight of the preparation. The numerical values are all percentages by weight, based on the total weight of the preparation, unless expressly indicated otherwise.

EXAMPLES

Example 1

Material:

| | |
|---|---|
| A. 50 mM HEPES buffer pH 8.32 | 50.00% |
| B. Montanide ISA 206 | 49.95% |
| C. Triethylamine (TEA) | 0.05% |

The following devices were used:
2 glass vessels 1,2 each of 2 l
peristaltic pump 3 Verder SF1500
HPLC pump 4
membrane module 5
membrane 6 Inocermic pore size 1.0 μm
3-way valve 7
hoses, hose connections
heat exchanger 8
product container 9, glass vessel 2 l The following plant was used according to the scheme in FIG. 1 on a laboratory scale:

The oil phase 1, which comprises the TEA, and the aqueous phase 2 consisting of HEPES buffer are heated to 33° C. After this temperature has been attained, the two phases are brought into contact with one another via a ceramic membrane 6, which is located in a case 5 called module, with a pore diameter of 1.0 μm, and circulated by pumps 3 and 4 until all of the aqueous phase has been combined with the oil phase. After the so-called membrane emulsification, the resulting W/O emulsion is passed, by means of a valve 7, over a heat exchanger 8, where it is cooled to 4° C., during which phase inversion takes place. The cooling rate is 2.5 K/min. The resulting multiple W/O/W emulsion is collected in the product container 9.

It has droplets with a drop diameter of 2.3 μm.

The complete experimental parameters are given in Table 1.

Figure 2:
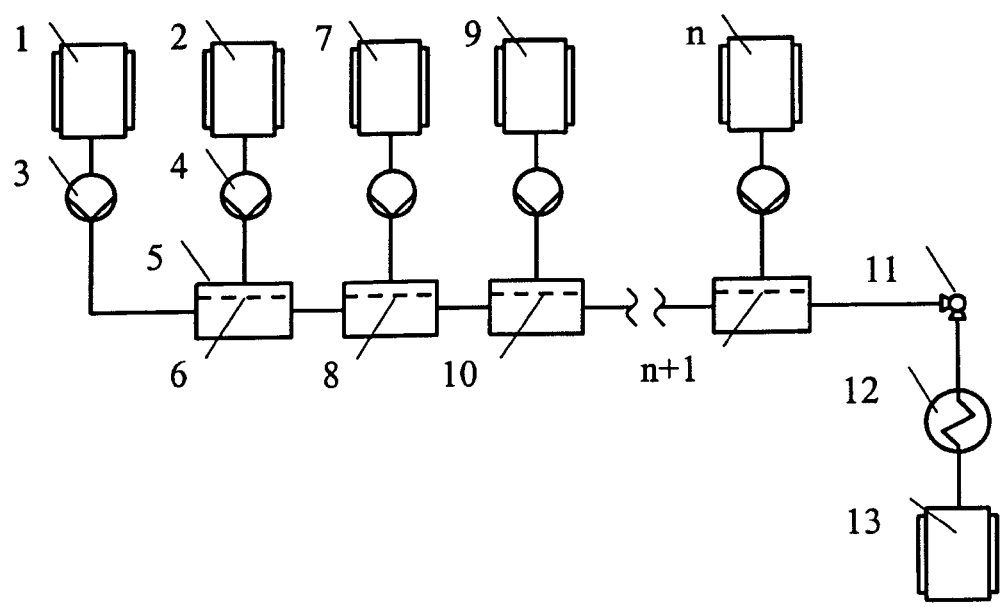

FIG. 2 shows a modified plant for incorporating a multitude n of active ingredients. In this, a continuous phase 1 is passed via a pump 3 behind one another through a plurality of membrane modules 5. This phase may be heat-treated. After the desired temperature has been attained, various, likewise heatable, discontinuous phases 2, 7, 9, n can be emulsified with various active ingredients and electrolytes through the membranes 6, 8, 10, n+1, which may differ with regard to material and pore size. By means of valve 11, the W/O emulsion formed can be passed over a heat exchanger 12 where it is heat-treated again in order to induce phase inversion. The resulting emulsion can be collected in product container 13.

Example 2

Material:

| | |
|---|---|
| A. 50 mM HEPES buffer pH 8.32 | 48.50% |
| B. MKS concentrate (monovalent) | 1.50% |
| C. Montanide ISA 206 | 49.95% |
| D. Triethylamine (TEA) | 0.05% |

The following devices were used:

Comparative Example 1

Membrane 6 Inocermic Pore Size 1.0 μm

The aqueous phase consisting of HEPES buffer with the MKS concentrate and the oil phase which comprises the TEA are heated to 33° C. Upon reaching 33° C., the two phases are brought into contact with one another via a ceramic membrane with a pore diameter of 1.0 μm and circulated until all of the aqueous phase has been combined with the oil phase. The resulting W/O emulsion is cooled over a heat exchanger to 4° C., during which phase inversion takes place. The cooling rate is 2.5 K/min. The resulting multiple W/O/W emulsion has droplets with a droplet diameter of 2.0 μm. Favourable experimental parameters correspond to Example 1 and Table 1.

Example 3

Material:

| | |
|---|---|
| A. 50 mM HEPES buffer pH 8.32 | 45.50% |
| B. MKS concentrate (trivalent) | 4.50% |
| C. Montanide ISA 206 | 49.95% |
| D. Triethylamine (TEA) | 0.05% |

The following devices were used:

Comparative Example 1

Membrane 6 Inocermic Pore Size 3.0 μm

The aqueous phase consisting of HEPES buffer with the MKS concentrate and the oil phase which comprises the TEA are heated to 33° C. Upon reaching 33° C., the two phases are brought into contact with one another via a ceramic membrane with a pore diameter of 3 μm and circulated until all of the aqueous phase has been combined with the oil phase. The resulting W/O emulsion is cooled to 4° C. over a heat exchanger, during which phase inversion takes place. The cooling rate is 2.3 K/min. The resulting multiple W/O/W emulsion has droplets with a droplet diameter of 2.0 μm.

The complete experimental parameters are given in Table 1.

Example 4

Material:

| | |
|---|---|
| A. 50 mM HEPES buffer pH 8.32 | 45.50% |
| B. MKS concentrate (monovalent) | 4.50% |
| C. Montanide ISA 206 | 49.95% |
| D. Triethylamine (TEA) | 0.05% |

The following devices were used:

Comparative Example 1

Membrane 6 Inocermic Pore Size 3.0 μm

The entire experimental plant was steam-sterilized beforehand at 121° C. for 30 min, and the experiment was conducted under absolute sterile conditions. The further course of the experiment corresponds to Example 3. The cooling rate is 1.4 K/min. The membrane used has a pore diameter of 3 μm. The resulting multiple W/O/W emulsion has droplets with a drop diameter of 2.0 μm. Subsequent injection into the animal gave an effectiveness of 100% based on the effectiveness of the vaccine prepared using the conventional process.

The complete experimental parameters are given in Table 1.

TABLE 1

| | Experimental parameters for Examples 1 to 4 | | | | | | |
|---|---|---|---|---|---|---|---|
| | Pore size | | Volumetric flow rate | | Temperatures | | Pressure |
| Example | $D_p$ membrane μm | Membrane area $cm^3$ | Pump 1 l/min | Pump 2 ml/min | continuous phase ° C. | after cooling ° C. | transmembrane bar |
| 1 | 1.0 | 47 | 3.4 | 80 | 31.3 | 3.2 | 1.2 |
| 2 | 1.0 | 47 | 3.4 | 80 | 34.5 | 3.9 | 1.9 |
| 3 | 3.0 | 47 | 3.4 | 80 | 33.8 | 4.7 | 3.5 |
| 4 | 3.0 | 47 | 3.4 | 80 | 31.4 | 4.3 | 3.5 |

The invention claimed is:

1. Process for the preparation of storage-stable, multiple emulsions of the water/oil/water (W/O/W) type which comprise one or more active ingredients with the steps
   a) stirring the active ingredient into an aqueous phase comprising a substance selected from the group consisting of boric acid, phosphoric acid, N-2-(acetamido)-2-aminoethanesulphonic acid, N-2-(acetamido)-2-iminodiacetic acid, alanine, 2-amino-2-methyl-1,3-propanediol, ammonia, N,N-bis(2-hydroxyethyl)-2-aminoethanesulphonic acid, N,N-bis(2-hydoxyethyl) glycine, 2,2-bis(hydroxyethyl)iminotris(hydroxymethyl)methane, 2-(cyclohexylamino) ethanesulphonic acid, 3-[4-(2-hydroxyethyl)1-piperazinyl]-propanesulphonic acid, histidine, imidazole, lactic acid, 2-morpholinoethane-sulphonic acid, 2-morpholinopropanesulphonic acid, piperazine-1,4-bis(2-ethane-sulphonic acid), N[tris(hydroxymethyl)methyl]-2-aminoethanesulphonic acid, N-[tris(hydroxymethyl)methyl] glycine, triethaneolamine, tris(hydroxymethyl)amino-methane, 2-[4-(2-hydroxyethyl)piperazin- 1-yl] ethanesulfonic acid, and citric acid,
   b) emulsifying the aqueous phase by passing the aqueous phase through a porous membrane having a pore size of 0.2 to 5 μm into an oil phase comprising a mineral oil, white oil, or vegetable oil, wherein the aqueous and oil phases are heated to a temperature of from 30° C. to 35° C. before said emulsification, and
   c) phase inversion of the heated emulsion from b), by cooling the mixture at a cooling rate of at least 0.3 K/min, where a non-ionic emulsifier is added to the oil phase in b).

2. Process according to claim 1, wherein the membrane is a porous inorganic membrane.

3. Process according to claim 1, wherein the phase inversion according to step c) is carried out at a cooling rate of at least 1 K/min.

4. Process according to claim 1, wherein the pressure difference over the membrane is $0.5*10^5 Pa$ to $25*10^5 Pa$.

5. Process according to claim 1, wherein the process is carried out continuously.

6. Process according to claim 1, wherein the active ingredient is a pharmaceutically active ingredient.

7. Process according to claim 6, wherein the active ingredient comprises an antigen or a preparation which comprises a peptide chain.

8. Process according to claim 1, wherein said membrane is a ceramic membrane.

9. Process according to claim 8, wherein said ceramic membrane comprises aluminum oxide, zirconium oxide and/or titanium oxide.

10. Process according to claim 1, wherein the pore size of the membrane is 0.3 to 3 μm.

11. Process according to claim 6, wherein said active ingredient comprises an active ingredient for veterinary purposes.

12. Process according to claim 6, wherein said active ingredient comprises an antigen for vaccine formulation.

13. Process according to claim 7, wherein said antigen comprises a virus or a microorganism and said peptide chain comprises a protein or a glycoprotein.

14. Process according to claim 6, wherein the active ingredient comprises at least one of a bacterium, a parasite, a glycoprotein which has been obtained from a microorganism, a synthetic peptide, and/or a protein or peptide which has been prepared by genetic manipulation.

15. Process according to claim 1, wherein the pressure difference over the membrane is $0.5*10^5 Pa$ to $5*10^5 Pa$.

16. Process according to claim 1, wherein the aqueous phase comprises 2-[4-(2-hydroxyethyl)piperazin-1-yl] ethanesulfonic acid.

17. Process according to claim 1, wherein the oil phase comprises mineral oil.

18. Process according to claim 1, wherein the non-ionic emulsifier comprises triethylamine.

* * * * *